(12) United States Patent
Stumber

(10) Patent No.: US 8,979,796 B2
(45) Date of Patent: Mar. 17, 2015

(54) APPLICATOR FOR TREATING SKIN

(75) Inventor: Michael Stumber, Korntal-Muenchingen (DE)

(73) Assignee: Robert Bosch GmbH, Stuttgart (DE)

( * ) Notice: Subject to any disclaimer, the term of this patent is extended or adjusted under 35 U.S.C. 154(b) by 469 days.

(21) Appl. No.: 13/260,850

(22) PCT Filed: Jan. 29, 2010

(86) PCT No.: PCT/EP2010/051089
§ 371 (c)(1),
(2), (4) Date: Sep. 28, 2011

(87) PCT Pub. No.: WO2010/112244
PCT Pub. Date: Oct. 7, 2010

(65) Prior Publication Data
US 2012/0022448 A1  Jan. 26, 2012

(30) Foreign Application Priority Data
Mar. 31, 2009  (DE) .................. 10 2009 002 019

(51) Int. Cl.
*A61M 5/00* (2006.01)
*A61M 35/00* (2006.01)
*A61M 37/00* (2006.01)

(52) U.S. Cl.
CPC ......... *A61M 35/003* (2013.01); *A61M 37/0015* (2013.01); *A61M 2037/0023* (2013.01); *A61M 2037/0061* (2013.01)
USPC ....................................................... 604/116

(58) Field of Classification Search
CPC ............. A61B 5/1411; A61B 5/14532; A61B 5/15146; A61B 5/1427; A61B 5/15186; A61B 5/150412; A61B 5/15142
USPC ........................ 604/272, 21, 22, 116; 600/583
See application file for complete search history.

(56) References Cited

U.S. PATENT DOCUMENTS

| | | | |
|---|---|---|---|
| 2,820,023 A * | 1/1958 | Cavanaugh et al. | 528/276 |
| 5,402,798 A * | 4/1995 | Swierczek et al. | 600/583 |
| 5,709,699 A * | 1/1998 | Warner | 606/181 |
| 5,830,170 A * | 11/1998 | Whiteman et al. | 604/1 |
| 6,562,014 B2 * | 5/2003 | Lin et al. | 604/317 |
| 2004/0058882 A1 * | 3/2004 | Eriksson et al. | 514/44 |
| 2007/0051362 A1 * | 3/2007 | Sullivan et al. | 128/200.23 |
| 2007/0161964 A1 * | 7/2007 | Yuzhakov | 604/272 |
| 2008/0195033 A1 * | 8/2008 | Eagleson et al. | 604/21 |
| 2011/0230736 A1 * | 9/2011 | Tepper et al. | 600/309 |

FOREIGN PATENT DOCUMENTS

| DE | 10 2004 032 892 | 2/2006 |
|---|---|---|
| JP | 2002-517358 A | 6/2002 |

(Continued)

OTHER PUBLICATIONS

International Search Report corresponding to PCT Application No. PCT/EP2010/051089, mailed Apr. 19, 2010 (German and English language document) (8 pages).

*Primary Examiner* — Nicholas Lucchesi
*Assistant Examiner* — Diva K Chander
(74) *Attorney, Agent, or Firm* — Maginot, Moore & Beck LLP

(57) ABSTRACT

An applicator for treating skin, includes a housing, in which a device for perforating an area of skin is arranged, wherein the device for perforating the skin can be brought into contact with the area of skin through an opening in the housing. At least one device for disinfecting is additionally arranged in the housing, and the device for disinfecting acts upon the area of skin through the same opening. With the applicator, a particularly secure and simple handling can be achieved.

11 Claims, 3 Drawing Sheets

(56) References Cited

FOREIGN PATENT DOCUMENTS

| | | | |
|---|---|---|---|
| JP | 2005-525141 A | 8/2005 |
| JP | 2006-346129 A | 12/2006 |
| WO | 99/63934 | 12/1999 |
| WO | 2008/062032 | 5/2008 |

* cited by examiner

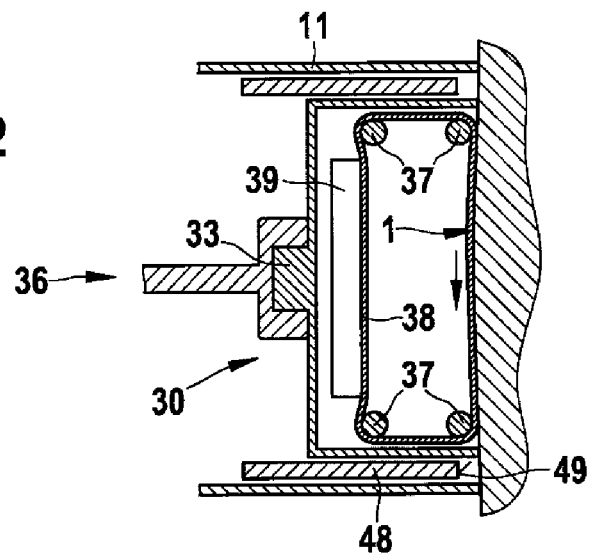
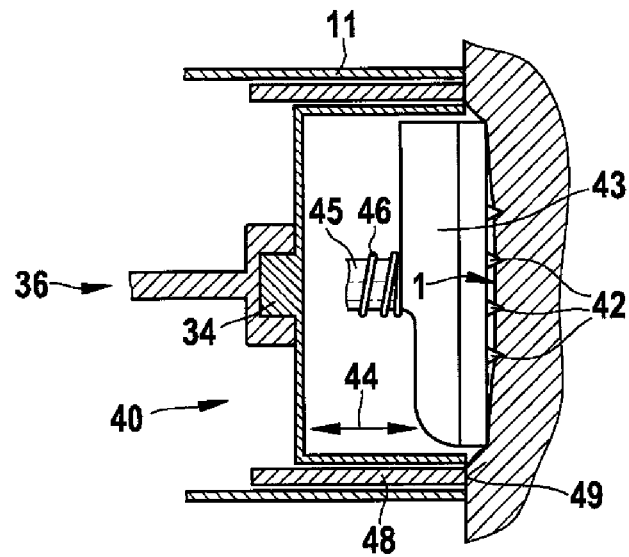

APPLICATOR FOR TREATING SKIN

This application is a 35 U.S.C. §371 National Stage Application of PCT/EP2010/051089, filed on Jan. 29, 2010, which claims the benefit of priority to Application Serial No. DE 10 2009 002 019.5, filed on Mar. 31, 2009 in Germany, the disclosures of which are incorporated herein by reference in their entirety.

BACKGROUND

The disclosure relates to an applicator for treating skin.

Such an applicator is known from DE 10 2004 032 892 A1. The known applicator has a needle plate, which can be actuated by means of a lifting device and with which the skin, in the area where an active-substance patch is later to be applied for example, is multiply perforated in order to form passages for the active substances stored in the active-substance patch. With active-substance patches of this kind, the active substances can pass through the skin and into the body as long as the passages are open. The self-healing process of the body means that the passages close again independently, for example after a few hours. The needles that are used in this context are in particular so-called micro-needles which, with the correct dimensions, cause almost no pain during perforation.

Micro-needles that are made of porous silicon or of biodegradable polymer and that can remain in the skin are also known from the prior art. The material, suitably produced, is automatically slowly decomposed by the intracellular liquid of the body such that, with micro-needles of this kind, the passages allow the active substance to pass through for about 2 to 3 days.

A problem when using certain known applicators is that the use of active-substance patches, for example, requires preparation and/or disinfection of the skin at the area to be perforated, so as to avoid infections of the perforated area of skin. The area of skin to be perforated is usually disinfected manually, for example using a swab soaked with disinfectant, and errors can arise both as regards the position of the subsequently perforated area of skin and also as regards the correct amount of disinfectant. Moreover, a high degree of spatial precision is also needed when applying the active-substance patch, so as to ensure that the active substances of the active-substance patch can penetrate as completely as possible into the skin.

SUMMARY

The object of the disclosure is therefore to develop an applicator for treating skin in such a way that handling is made easier, for example when using active-substance patches, and at the same time at least the risk of infections is reduced. This object is achieved in an applicator having the features set forth herein. The disclosure is based on the concept that the steps of disinfecting and perforating the area of skin are carried out in succession using one and the same applicator, without this requiring the applicator to be placed several times onto the area of skin that is to be treated. In this way, a very high degree of positioning accuracy is achieved as regards the different treatments of the area of skin. This means that an applicator according to the disclosure, in addition to having the device for perforating the area of skin, also has at least a device for disinfecting the area of skin, which disinfecting device acts on the area of skin to be treated by way of the same opening in the housing. This ensures that, in the required manner, the area of skin to be perforated is prepared optimally for the subsequent perforation, both as regards the site of the disinfection and also as regards the amount of disinfectant and the execution of the disinfection, as a result of which subsequent infections can be avoided.

Advantageous developments of the applicator according to the disclosure for treating skin are set forth in the dependent claims. All combinations of at least two of the features disclosed in the description, in the claims and/or in the figures fall within the scope of the disclosure.

In a preferred embodiment of the applicator, a control device is provided, which controls the perforating device and the disinfecting device independently in accordance with at least one stored program sequence, and means are provided which, in accordance with the program sequence, bring the perforating device and the disinfecting device into operative contact with the area of skin through the opening of the housing. In this way, the treatment steps can proceed completely automatically, thereby permitting a particularly simple and error-free operation of the applicator.

In another embodiment of the disclosure, a device for applying an active-substance patch to the previously disinfected and perforated area of skin is additionally provided, and the device for applying an active-substance patch can likewise be controlled automatically by the control device. By means of this embodiment, active-substance patches can be applied to the previously disinfected and perforated area of skin automatically and with precise positioning, such that handling errors are avoided in this respect too.

The design of the disinfecting device can be made relatively simple by having a carrier which is treated by means of a disinfectant and which is movable with surface contact across the area of skin to be disinfected.

In terms of its design, provision is advantageously made that the carrier is band-shaped, that the carrier, on the outer face thereof coming into contact with the area of skin, has an absorbent material, and that a reservoir for the disinfectant is provided, via which reservoir the outer face can be wetted with disinfectant. In this way, the disinfecting device has a long useful life and works particularly reliably.

When manually applying an active-substance patch, it is particularly advantageous, for the purpose of positionally accurate placement of the active-substance patch, if a marking device is provided which peripherally surrounds the disinfecting device or the perforating device and can be brought into surface contact with the area of skin in order to visually identify the extent of the area of skin.

In order to perforate the area of skin, provision is additionally made that the perforating device has a perforating punch with a multiplicity of micro-needles arranged alongside one another. A perforating punch of this kind has a compact structure, permits reliable perforation of the area of skin and has a long useful life.

Alternatively, and in order to obtain passages in the area of skin that close again only after quite a long time, provision is also made, in one development, that the perforating device has a multiplicity of micro-needles which are arranged on a carrier, and that the micro-needles are designed as self-disintegrating micro-needles, which are detachable from the carrier. The micro-needles can in this case be made, for example, of porous silicon or biodegradable polymer.

In order to bring at least the disinfecting device and the perforating device into the area of the opening of the housing, provision is made, in a structurally advantageous embodiment, that a support device is arranged in the housing, and that the perforating device and the disinfecting device can be pivoted into the area of the opening by means of the support device.

It is also particularly advantageous if at least the perforating device and the disinfecting device are arranged exchangeably on the support device. This means that these devices can be easily replaced at the end of their useful life or in order to refill disinfectant, with the result that the applicator has a particularly long operating life and can be used again and again.

BRIEF DESCRIPTION OF THE DRAWINGS

Further advantages, features and details of the disclosure will become clear from the following description of preferred illustrative embodiments and from the drawings, in which:

FIG. 2 shows, in a longitudinal section, a partial area of the applicator according to FIG. 1 during disinfection of an area of skin, FIG. 3 shows, in a longitudinal section, a partial area of the applicator according to FIG. 1 during perforation of the area of skin disinfected in FIG. 2.

DETAILED DESCRIPTION

Figure 1:
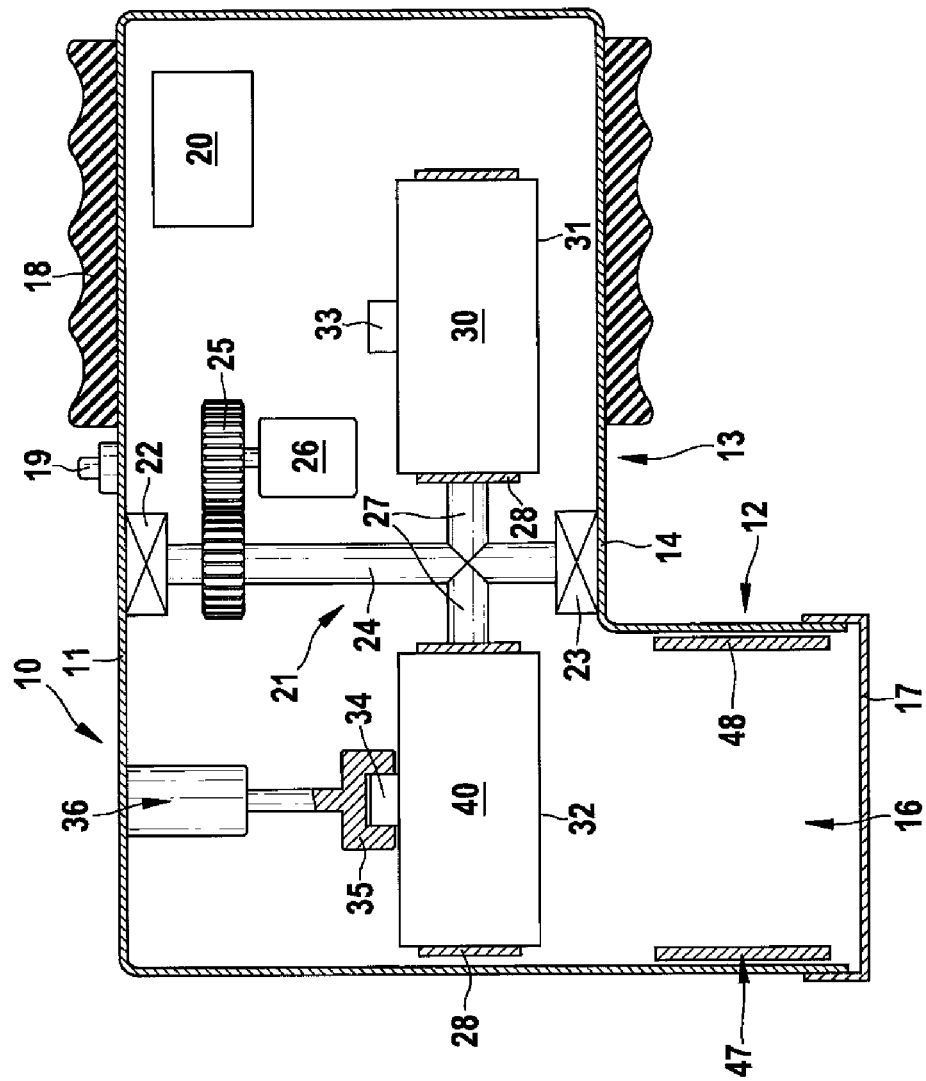
FIG. 1 shows, in a simplified longitudinal section, an applicator for treating skin.
Figure 5:
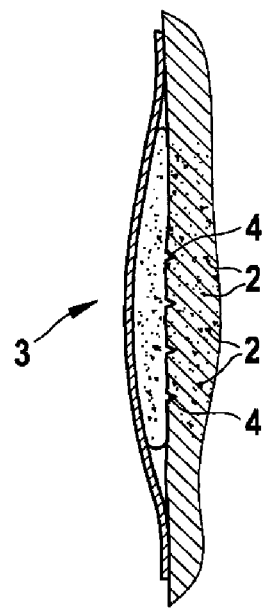
FIG. 5 shows, in section, the previously disinfected and perforated area of skin after application of an active-substance patch.

FIG. 1 depicts an applicator 10 for treating an area of skin 1, in particular an area of skin 1 of a human. An active-substance patch 3 containing medical active substances 2 is intended to be applied to the area of skin 1 and release its active substances 2 into the human body through passages or perforations 4 formed in the area of skin 1 (FIG. 5). The applicator 10 here serves at least to prepare the area of skin 1, such that the active-substance patch 3 can be applied to the area of skin 1 in exactly the right position.

The applicator 10 has a housing 11 with a first area 12, of which the cross section is in particular rectangular or square and on the side of which a second area 14 designed as a handle 13 is integrally formed, such that, in cross section, the housing 11 has an approximately L-shaped configuration. The housing 11 has, on the side thereof coming into surface contact with the area of skin 1, an opening 16, which can be closed by means of a removable protective cover 17. An anatomically shaped molding 18 is arranged on the outer face of the handle 13, either as a separate structural part or integrally with the housing 11. By means of the molding 18, the applicator 10 can be held in one hand by an operator, who can also be the person to be treated. On the outer face of the housing 11, an actuating switch 19 is also arranged, which is electrically connected to a control device 20 arranged in the interior of the housing 11 of the applicator 10.

In the interior of the housing 11, the applicator 10 has, for example, a support device 21. The support device 21 comprises a shaft 24, which is mounted rotatably in two bearings 22, 23 and which is rotatable via a toothed wheel 25 and via a servomotor 26 that can be controlled by the control device 20. Support arms 27, arranged in particular at uniform angular intervals, are connected to and rotate with the shaft 24, and functional units 30, 40 are arranged at the outer ends of the support arms 27, in each case in a holder 28.

The functional units 30, 40, designed as devices for respectively disinfecting and perforating the area of skin 1, each have their own respective housing 31, 32 which, on the upper face thereof, has an adapter 33, 34 that engages with a correspondingly shaped mating piece 35 of a lifting mechanism 36. By means of the lifting mechanism 36, the corresponding functional unit 30, 40 controlled by the control device 20 can be removed from the holder 28 and moved into the area of the opening 16 of the housing 11 and back again. The functional units 30, 40 each serve for a particular treatment of the area of skin 1. Thus, the first functional unit 30 is used to disinfect the area of skin 1, while the second functional unit 40 is used to perforate the area of skin 1.

As can best be seen from FIG. 2, the first functional unit 30 has, within its housing 31, a plurality of rotatably mounted rollers 37, at least one of which rollers 37 can be driven by means of a drive mechanism (not shown). A band-shaped carrier 38 for a disinfectant stretches around the rollers 37. The carrier 38, at least on the outer face thereof coming into contact with the area of skin 1, is made of absorbent material, for example fleece, padding or the like. On the face of the carrier 38 lying opposite the opening 16, the carrier 38 is operatively connected to a reservoir 39 for the disinfectant. The disinfectant is a standard disinfectant used for disinfecting skin, for example ethanol. The face of the carrier 38 directed toward the reservoir 39 is wetted or saturated with the disinfectant from said reservoir 39.

As can be seen from FIG. 3, the second functional unit 40 has a perforating punch 43 for the area of skin 1, which perforating punch 43 is provided with a multiplicity of microneedles 42 arranged alongside one another. The perforating punch 43 is axially movable, in the direction of the double arrow 44, within its housing 32 open on the side directed toward the opening 16. When used on the area of skin 1, this means that the perforating punch 43 moves substantially perpendicularly with respect to the area of skin 1. The perforating punch 43 has a shaft 45, which is enclosed by a compression spring 46. By means of the force of the compression spring 46, the perforating punch 43, with its perforating microneedles 42, is pressed with a defined force (for example because the compression spring 46 is suitably pretensioned) against the area of skin 1 in order to perforate it. As an alternative to this, it is also possible that the movement of the perforating punch 43 for carrying out the perforation is executed either via the lifting mechanism 36 or via another suitable mechanism, particularly one arranged integrally in the functional unit 40. If appropriate, additional sensors, for example optical sensors, can also be provided, which ensure that the area of skin 1 has been perforated in the right way.

Moreover, provision can additionally be made that, inside the housing 11 in the area of the opening 16, the perforating punch 43 is surrounded about its circumference by a marking device 47. The marking device 47 has a marking frame 48, of which the front face 49 directed toward the opening 16 is treated with a skin-compatible dye which, upon contact with the area of skin 1, transfers itself onto the area of skin 1. The movement of the marking frame 48 is preferably coupled to the perforating punch 43.

Alternatively, instead of using a marking device 47, it is also possible to dye the disinfectant such that, when the area of skin 1 is being disinfected by means of the carrier 38, the disinfectant is transferred onto the area of skin 1 and identifies the disinfected area of skin 1 by a color.

Figure 4:
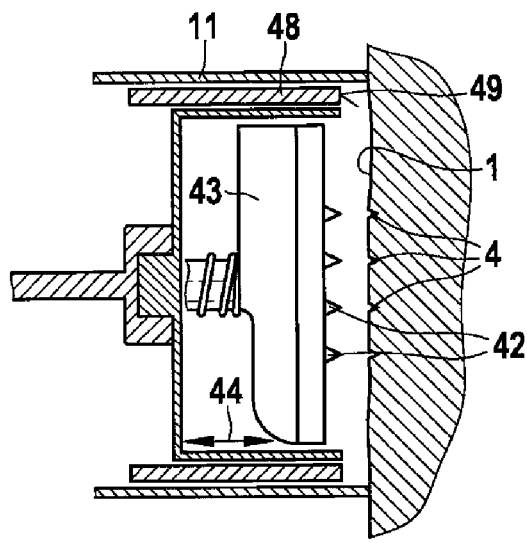
FIG. 4 shows, in a longitudinal section, a partial area of the applicator according to FIG. 3 after perforation of the area of skin.

The mode of operation of the applicator 10 is explained as follows. In a first step, the operator manually places the applicator 10 with the opening 16 thereof onto the area of skin 1 that is to be perforated. As soon as this is done, the operator presses the actuating switch 19. This causes the start-up of an automatically running program in the control device 20. A first program step of said program provides that the first functional unit 30 serving to disinfect the area of skin 1 is triggered. By means of the lifting mechanism 36, this functional unit 30 is brought into surface contact with the area of skin 1 according to FIG. 2, after which the carrier 38 saturated with disinfectant is set in motion by means of the at least one driven roller 37, and this has the effect of disinfecting the entire surface of the area of skin 1 by means of the carrier 38 sliding across the area of skin 1. Then, in a second program step, the second functional unit 40 with the perforating punch 43 and with the marking device 47 is triggered by the control device 20. According to FIG. 3, these cause perforation of the area of skin 1, such that the perforations 4 are formed within the previously disinfected area of skin 1. At the same time, the perforated area is identified in color by means of the marking device 47 and is therefore then visually discernible to the operator. As soon as this is done, the operator can remove the applicator 10 from the area of skin 1 (FIG. 4) and, in a final step, apply the active-substance patch 3 in the exact position onto the area of skin 1 previously identified by the dye (FIG. 5). The active substances 2 can now pass from the active-substance patch 3 into the body through the perforations 4.

It will further be noted that the abovementioned steps (without the application of the active-substance patch 3) of disinfecting and perforating can be repeated at the same site in order to achieve more intense treatment. Alternatively, however, the treatment can also be repeated on, for example, directly contiguous areas of skin 1, in order to treat a larger skin surface.

Moreover, in the illustrative embodiment described above, the active-substance patch 3 is applied manually to the area of skin 1 by the operator. Such a procedure is expedient if the applicator 10 is intended to be used for different active-substance patches 3. However, in a modification of the illustrative embodiment described above, it is also possible to design the applicator 10 in such a way that one or more additional functional units are arranged in the applicator 10 analogously to the functional units 30 and 40. These additional functional units are then, like the functional units 30, 40, also arranged exchangeably or replaceably on the support device 21. In each of these additional functional units, for example, a defined number of active-substance patches (of different formats) can be stored which, after activation via the control device 20, are applied fully automatically to the previously disinfected and perforated area of skin 1. In this case, of course, it is possible to do without a marking device 47. In an applicator 10 that has been modified in this way, all the steps are therefore triggered fully automatically after activation of the actuating switch 19 (or of modified operating elements via which, for example, different patch formats or treatment courses can be selected). Moreover, the applicator 10 can also be modified such that, instead of the functional unit 40 with the micro-needles 42 and the perforating punch 43, use is made of a functional unit that has micro-needles made of porous silicon or of biodegradable polymer. After penetrating the skin, these micro-needles are detached from a carrier by means of a suitable device and thereafter remain in the skin until the intercellular liquid slowly breaks them up.

Of course, the mechanical set-up of the applicator 10 can deviate greatly from the described illustrative embodiment. In particular, the functional units 30, 40 for disinfecting and perforating can be designed and controlled in other ways.

The invention claimed is:

1. An applicator for treating skin, comprising:
a housing defining an opening;
a perforating device arranged in the housing, said perforating device configured to be advanced through the opening and into contact with an area of the skin located outside of said housing to perforate the area of the skin;
at least one disinfecting device arranged in the housing, said at least one disinfecting device being configured to act on the area of skin through the opening;
a control device configured to control the perforating device and the disinfecting device independently in accordance with at least one stored program sequence; and
a mechanism configured to advance the perforating device and the disinfecting device into operative contact with the area of skin through the opening of the housing in accordance with the at least one stored program sequence.

2. The applicator as claimed in claim 1, wherein the disinfecting device has a carrier treated by a disinfectant and which is movable with surface contact across the area of skin to be disinfected.

3. The applicator as claimed in claim 2, wherein:
the carrier is band-shaped,
the carrier, at least on an outer face thereof coming into contact with the area of skin, has an absorbent material,
the applicator further comprises a reservoir configured to contain the disinfectant, and
the outer face of the carrier is configured to be wetted with the disinfectant.

4. The applicator as claimed in claim 2, wherein the disinfectant is dyed and, upon contact with the area of skin is configured to identify the area of skin by color.

5. The applicator as claimed in claim 1, further comprising a marking device which peripherally surrounds at least one of the disinfecting device and the perforating device and is configured to be brought into surface contact with the area of skin in order to visually identify the extent of the area of skin.

6. The applicator as claimed in claim 1, wherein the perforating device has a perforating punch with a multiplicity of micro-needles arranged alongside one another.

7. An applicator for treating skin, comprising:
a housing defining an opening;
a perforating device arranged in the housing, said perforating device configured to be advanced through the opening and into contact with an area of the skin located outside of said housing to perforate the area of the skin;
at least one disinfecting device arranged in the housing, said at least one disinfecting device being configured to act on the area of skin through the opening; and
an applicator device configured to apply an active-substance patch to the previously disinfected and perforated area of skin,
wherein the applicator device is configured to be controlled automatically by a control device.

8. The applicator as claimed in claim 7, wherein:
the control device is configured to control the perforating device and the disinfecting device independently in accordance with at least one stored program sequence, and
the applicator further comprises a mechanism configured to advance the perforating device and the disinfecting device into operative contact with the area of skin through the opening of the housing in accordance with the at least one stored program sequence.

9. An applicator for treating skin, comprising:
a housing defining an opening;
a perforating device arranged in the housing, said perforating device configured to be advanced through the opening and into contact with an area of the skin located outside of said housing to perforate the area of the skin; and at least one disinfecting device arranged in the housing, said at least one disinfecting device being configured to act on the area of skin through the opening, wherein:

the perforating device has (i) a multiplicity of micro-needles, and (ii) a carrier on which the multiplicity of micro-needles are arranged, and the micro-needles are designed as self-disintegrating micro-needles, which are detachable from the carrier.

10. An applicator for treating skin, comprising:

a housing defining an opening;

a perforating device arranged in the housing, said perforating device configured to be advanced through the opening and into contact with an area of the skin located outside of said housing to perforate the area of the skin;

at least one disinfecting device arranged in the housing, said at least one disinfecting device being configured to act on the area of skin through the opening; and a support device arranged in the housing and configured to hold at least the perforating device and the disinfecting device, wherein the perforating device and the disinfecting device are configured to be pivoted into the area of the opening with the support device.

11. The applicator as claimed in claim 10, wherein at least the perforating device and the disinfecting device are arranged exchangeably on the support device.

* * * * *